(12) United States Patent
Yoon et al.

(10) Patent No.: US 6,277,996 B1
(45) Date of Patent: Aug. 21, 2001

(54) THIAZOLE COMPOUND AND A PROCESS THEREOF

(75) Inventors: Dae-chul Yoon, Gunpo; Seung-won Yoo, Ansan; Dong Gyun Shin, Kyunggi-Do; Myoung Ki Lee, Seoul; Mi Soon Park; Yoon Seok Lee, both of Ansan; Yoon Seok Song, Shiheung, all of (KR)

(73) Assignee: Hanmi Fine Chemicals Co., Ltd., Kyunggi-Do (KR)

( * ) Notice: Subject to any disclaimer, the term of this patent is extended or adjusted under 35 U.S.C. 154(b) by 0 days.

(21) Appl. No.: 09/564,979

(22) Filed: May 4, 2000

(30) Foreign Application Priority Data

Mar. 6, 2000 (KR) .................................................. 00-11127

(51) Int. Cl.$^7$ .................................................. C07D 277/38
(52) U.S. Cl. .................................................. 548/194
(58) Field of Search .................................................. 548/194

(56) References Cited

U.S. PATENT DOCUMENTS

| 4,258,041 | 3/1981 | O'Callaghan et al. . |
| 4,433,141 | 2/1984 | Jones et al. . |
| 5,182,383 | 1/1993 | Prager et al. . |

FOREIGN PATENT DOCUMENTS

| 2 052 490 | 1/1981 | (GB) . |
| 98/31685 | 7/1998 | (WO) . |

*Primary Examiner*—Robert Gerstl
(74) *Attorney, Agent, or Firm*—Venable; Richard D. Schmidt

(57) ABSTRACT

The present invention relates to a new crystalline aminothiazole derivative represented by the following formula (I) which is very useful for the preparation of cephalosporin antibiotics, including ceftazidime and cefixime, etc:

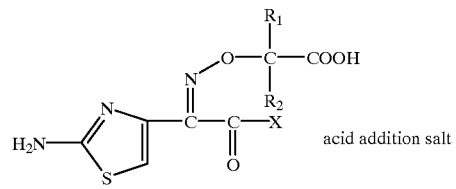

(I) acid addition salt wherein $R_1$ and $R_2$ are the same or different and independently represent H, an alkyl group of 1 to 4 carbon atoms, or a cycloalkyl group of 3 to 5 carbon atoms, X represents chlorine or bromine, and the acid in the acid addition salt represents an inorganic acid, such as hydrochloric acid, hydrobromic acid, sulfuric acid, or perchloric acid, or an organic acid, such as formic acid, acetic acid, trifluoroacetic acid, propionic acid, methanesulfonic acid, or benzenesulfonic acid.

8 Claims, 1 Drawing Sheet

THIAZOLE COMPOUND AND A PROCESS THEREOF

BACKGROUND OF THE INVENTION

1. Field of the Invention

The present invention relates to a new crystalline aminothiazole derivative represented by the following formula (I) and a process of preparing the same, which is very useful as an intermediate for the preparation of cephalosporin antibiotics, including ceftazidime and cefixime:

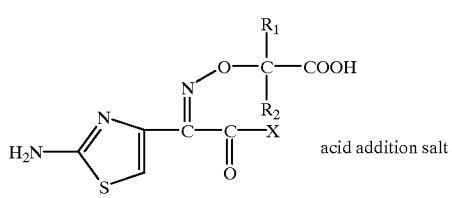

(I) acid addition salt wherein $R_1$ and $R_2$ are the same or different and independently represent H, an alkyl group of 1 to 4 carbon atoms, or a cycloalkyl group of 3 to 5 carbon atoms, etc., X represents chlorine or bromine, and the acid in the acid addition salt represents an inorganic acid, such as hydrochloric acid, hydrobromic acid, sulfuric acid, or perchloric acid, etc., or an organic acid, such as formic acid, acetic acid, trifluoroacetic acid, propionic acid, methanesulfonic acid, or benzenesulfonic acid, etc.

2. Description of the Prior Art

Many processes for the preparation of cephalosporin antibiotics were disclosed in literatures and patents. In such prior processes, generally, a 2-aminothiazol carboxylic acid compound of the following formula (I-1) is converted into its reactive derivative which is then acylated by reaction with an amino group of a 3-cephem compound to produce a cephem compound:

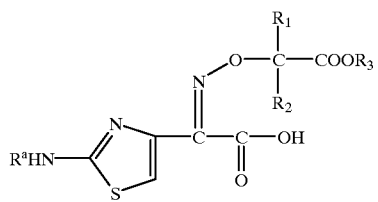

(I-1)

where $R_1$ and $R_2$ have the same meanings as described above, $R_3$ is a carboxy protecting group which is conventional in the art, $R^a$ is hydrogen or an amino protecting group.

The reactive derivative of the compound of the formula (I-1) includes, for example, an acid halide, a reactive ester, a reactive amide, or a mixed acid anhydride, etc. However, in the case of employing the acid halide as the reactive derivative, it is disadvantageous in that the preparation of the acid halide must be carried out under strict reaction conditions. In addition to this disadvantage, the compound of the formula (I-1) is first protected on the amino group of its thiazole ring and then converted into its reactive acid halide with an acid halogenating agent. Next, the protected compound is acylated as such with the acylating agent without being subjected to a separation step, such that an unwanted side reaction of the acid halide with the acylating agent is proceeded. For this reason, the use of the acid halide has another problem in that by-products are significantly produced. Moreover, with respect to a further particular problem with the use of the acid halide, as the acid halide is acylated in a state where its functional groups are protected, deprotection of the resulting product must be carried out after the acylation reaction.

On the other hand, in the case of carrying out the acylation with the reactive ester or reactive amide of the compound of the formula (I), the acylation produces a product in low yield. Moreover, as the reactive ester or amide is low in reactivity, the acylation requires a relatively long reaction time. Additionally, the by-products resulted from the acylation are difficult to be removed after the acylation, such that it is difficult for the desired product to be obtained at a high yield and purity.

SUMMARY OF THE INVENTION

We, therefore, have continued to conduct research in an attempt to solve the problems of the prior art. As a result of that, we have found a new intermediate represented by the formula (I) which has not been known up to date. Such a new compound was found to possess a pure crystalline form of acid halide, from which the protecting groups were removed. Thus, where the new compound was used in the acylation with the 3-cephem compound for the preparation of ceftazidime and cefixime, etc., the acylation was completed in a short period of time with little or no production of by-products, thereby allowing the desired compound to be prepared at a high yield and purity. Based on this fact, we have perfected the present invention.

It is therefore an object of the present invention to provide a new aminothiazole compound represented by the following formula (I) and a process of preparing the same, which is useful for the preparation of cephalosporin antibiotics, including ceftazidime, cefixime, and the like:

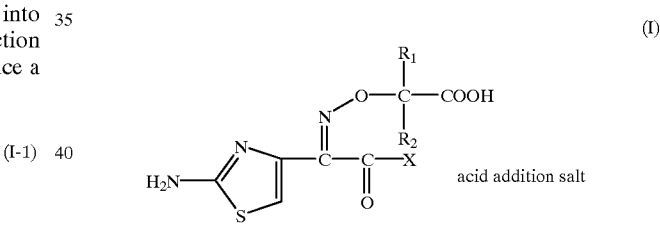

(I) acid addition salt wherein $R_1$ and $R_2$ are the same or different and independently represent H, an alkyl group of 1 to 4 carbon atoms, or a cycloalkyl group of 3 to 5 carbon atoms, etc., X represents chlorine or bromine, and the acid in the acid addition salt represents an inorganic acid, such as hydrochloric acid, hydrobromic acid, sulfuric acid, or perchloric acid, etc., or an organic acid, such as formic acid, acetic acid, trifluoroacetic acid, propionic acid, methanesulfonic acid, or benzenesulfonic acid, etc.

DETAILED DESCRIPTION OF THE PREFERRED EMBODIMENTS

Figure 1:
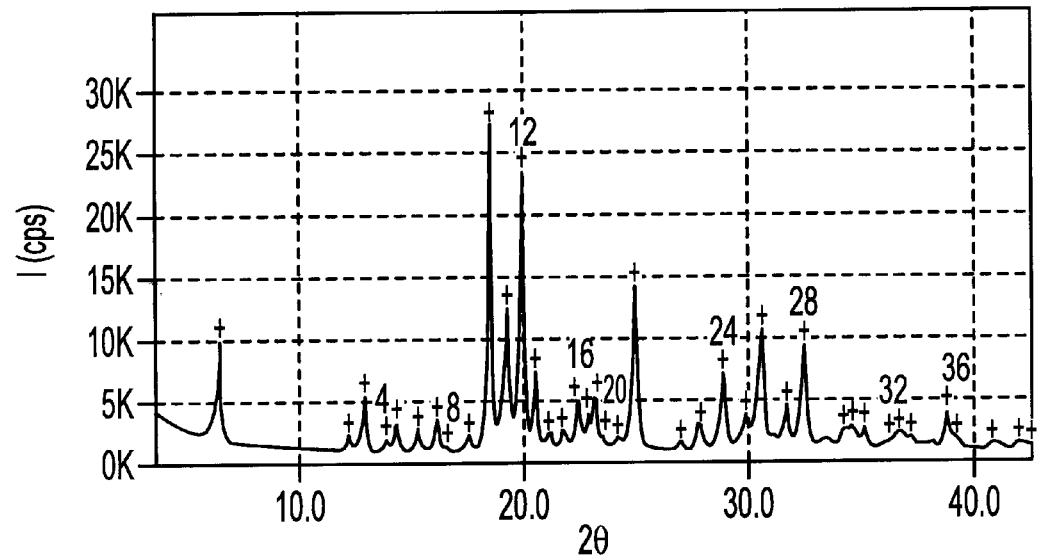
FIG. 1 shows a Debye-Scherrer X-ray powder diffraction spectrum of (Z)-2-(2-carboxyprop-2-oxyimino)-2-(2-aminothia zol-4-yl)acetylchloride monohydrochloride according to the present invention.

The foregoing and other objects, features and advantages of the invention will be apparent to those skilled in the art to which the present invention relates from reading the following specification.

Briefly, the new aminothiazole compound of the formula (I) of the present invention can be prepared according to the following reaction scheme:

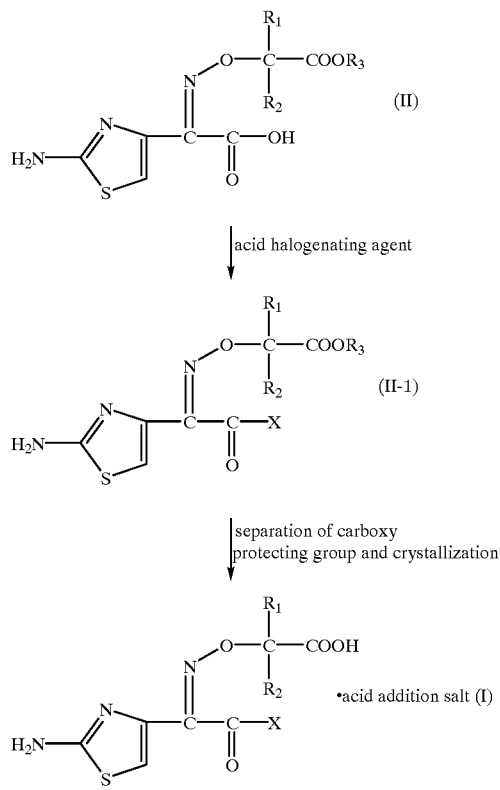

In the preparation of the new aminothiazole compound of the formula (I) according to the present invention, the organic acid of the above formula (II) can be synthesized using ethyl 2-amino-α-(hydroxyimino)-4-thiazol acetate generally known in the art, as a starting material, according to the conventional manner known in the art.

The starting material (II) is converted into an acid halide of the formula (II-1) from which the desired compound of the formula (I) is then obtained. For this purpose, the organic acid of the formula (II) is first treated with an acid halogenating agent, such as phosphorus pentachloride, phosphorus trichloride, or preferably, phosphorus oxychloride, etc., to produce the acid halide of the formula (II). Then, the reaction solution containing the acid halide (II) is treated with an organic or inorganic acid without being subjected to any separation step, such that the carboxy protecting group of the acid halide (II) is removed. Simultaneously with the removal of the carboxy protecting group, the acid chloride (II) is crystallized in such a manner that it has the form of the acid addition salt. The resulting crystalline material is filtered to remove the unnecessary impurities, thereby obtaining the desired crystalline compound (I) of a pure and stable form. If the compound (I) so obtained is used for the acylation with 7-aminocephalosporin derivative, the step of removing the carboxy protecting group as conducted in the prior art after the acylation becomes unnecessary. As a result, it is possible to prepare the cephalosporin derivative in a more economical way and at a high purity.

A solvent which can be used for preparing the compound of the formula (II-1) in the process according to the present invention includes, for example, methylene chloride, chloroform, diethyl ether, acetonitrile, 1,2-dichloromethane, acetone, or a combination thereof, etc. Among these solvents, it is preferred to use methylene chloride or a mixed solvent of methylene chloride and diethyl ether. Generally, the reaction for preparing the compound of the formula (II-1) is carried out at a temperature in the range of −20° C. to 30° C., and preferably in the range of 0° C. to 5° C.

The acid halogenating agent which can be used for the preparation of the acid halide of the formula (II-1) from the organic acid of the formula (II) includes, for example, phosphorus pentachloride, phosphorus trichloride, phosphorus oxytrichloride, thionyl chloride, oxalyl chloride, phosphorus tribromide, or sulfuryl chloride, etc. The preferred acid halogenating agent is phosphorus oxychloride.

Solvent which can be used in preparing the acid addition salt of the compound (I) from the acid halide of the formula (II) includes, for example, methylene chloride, chloroform, diethyl ether, acetonitrile, or 1,2-dichloroethane, etc., similarly with the case of preparing the compound (II-1). It is, however, preferred to use ether and a mixed solvent of ether and a halo-lower alkane.

Furthermore, the acid which is suitable for use in removing the carboxy protecting group of the compound (II) while making the compound (I) of the crystalline acid addition salt form includes, for example, an inorganic acid, such as anhydrous hydrochloric acid, anhydrous hydrobromic acid, anhydrous hydroiodic acid, perchloric acid, a dilution of chloric acid in diethyl ether, a dilution of anhydrous hydrochloric acid in acetic acid, a dilution of anhydrous hydrobromic acid in acetic acid, and sulfuric acid, etc., or an organic acid, such as formic acid, acetic acid, trifluoroacetic acid, propionic acid, methanesulfonic acid, benzenesulfonic acid, and p-toluenesulfonic acid, etc.

The acid used for such a hydrolysis may be suitably chosen depending on the nature of the protecting group to be removed. Occasionally, this hydrolysis may also be carried out in the presence of a cation trapping agent, such as mp-cresol, phenol, or anisole, etc. This reaction is carried out at a temperature in the range of −20° C. to 30, and preferably in the range of −5° C. to 10° C., similarly to the preparation of the acid halide (II).

Figure 2:
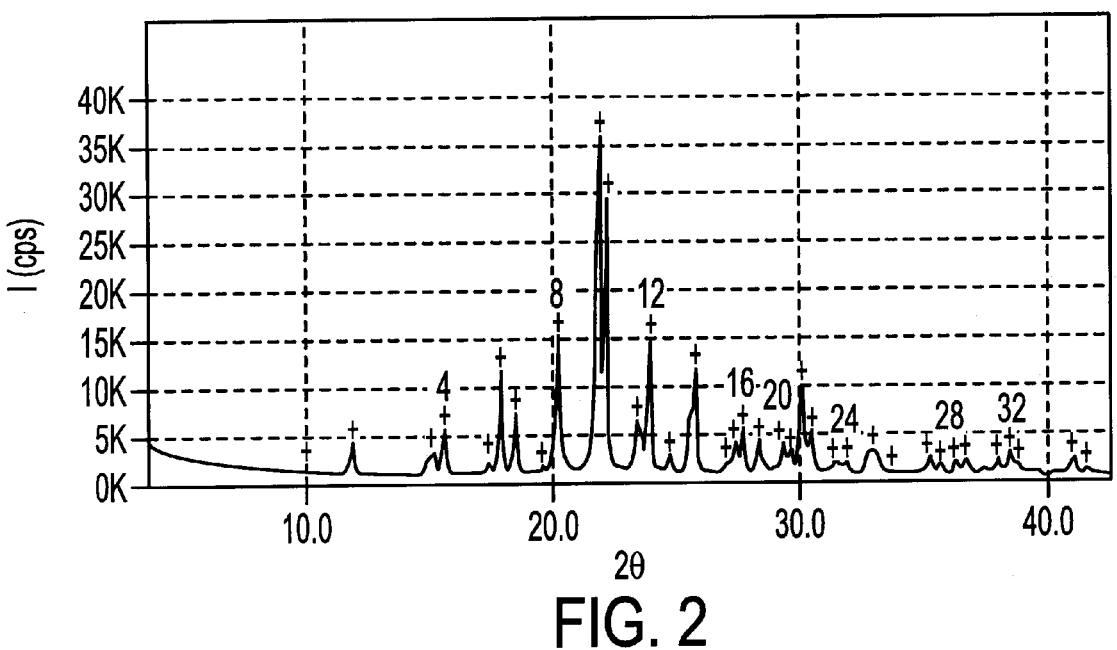
FIG. 2 shows a Debye-Scherrer X-ray powder diffraction spectrum of (Z)-2-(2-carboxymethoxyimino)-2-(2-aminothiazol-4-yl)acetylchloride monohydrochloride according to the present invention.

After removing the carboxy protecting group without the distillation and condensation of the reaction solution while naturally being deposited in the reaction solution, the resulting compound of the formula (I) is present in the form of a crystalline compound which can be easily separated and collected. The crystallinity of the compound (I) can be confirmed by measuring its X-ray diffraction. FIGS. 1 and 2 show a Debye-Scherrer X-ray powder diffraction spectrum of (Z)-2-(2-carboxyprop-2-oxyimino)-2-(2-aminothiazol-4-yl)acetylchloride monohydrochloride, and a Debye-Scherrer X-ray powder diffraction spectrum of (z)-2-(2-carboxymethoxyimino)-2-(2-aminothiazol-4-yl) acetylchloride monohydrochloride, respectively, that belong to the group of the compound (I). From the spectra in FIGS. 1 and 2, characteristic peaks of the crystalline compounds (I) can be confirmed. Moreover, Tables 1 and 2 below show Debye-Scherrer X-ray powder diffraction patterns inherent in the compound (I). In Tables 1 and 2, the symbol "2θ" represents the diffraction angle, "d" the interplanar spacing, and "I/I₀" the relative intensity.

TABLE 1

Debye-Scherrer X-ray powder diffraction spectrum of (Z)-2-(2-carboxyprop-2-oxyimino)-2-(2-aminothiazol-4-yl) acetylchloride monohydrochloride

| 2θ | d | I/I₀ |
|---|---|---|
| 6.46 | 13.67 | 297 |
| 12.88 | 6.87 | 173 |
| 16.10 | 5.50 | 103 |
| 18.52 | 4.79 | 1000 |
| 19.34 | 4.59 | 414 |
| 19.96 | 4.44 | 847 |
| 20.58 | 4.31 | 226 |
| 22.48 | 3.95 | 141 |
| 22.92 | 3.88 | 102 |
| 23.20 | 3.83 | 149 |
| 24.98 | 3.56 | 505 |
| 28.92 | 3.08 | 228 |
| 30.58 | 2.92 | 352 |
| 31.74 | 2.81 | 114 |
| 32.52 | 2.75 | 304 |
| 38.80 | 2.31 | 112 |

TABLE 2

Debye-Scherrer X-ray powder diffraction spectrum of (Z)-2-(2-carboxymethoxyimino)-2-(2-aminothiazol-4-yl) acetylchloride monohydrochloride

| 2θ | D | I/I₀ |
|---|---|---|
| 15.58 | 5.68 | 137 |
| 17.94 | 4.94 | 309 |
| 18.54 | 4.78 | 182 |
| 20.22 | 4.39 | 407 |
| 21.84 | 4.07 | 1000 |
| 22.16 | 4.01 | 811 |
| 23.46 | 3.79 | 153 |
| 23.96 | 3.71 | 389 |
| 25.82 | 3.45 | 309 |
| 27.76 | 3.21 | 130 |
| 30.12 | 2.96 | 252 |
| 30.50 | 2.93 | 121 |

The following examples are for illustration purposes only and in no way limit the scope of this invention.

EXAMPLE 1

Preparation of (Z)-2-(2-carboxyprop-2-oxyimino)-2-(2-aminothiazol-4-yl)acetylchloride monohydrochloride After cooling down a mixture of 2,000 ml of dichloromethane and 2,000 ml of diethyl ether to a temperature of 0° C. to 5° C., 55 ml of phosphorus oxychloride and 38 ml of N,N-dimethylformamide were sequentially added dropwise thereto. At the same temperature, the solution was stirred for 30 minutes, and 100 g of (Z)-2-(2-t-butoxycarbonylprop-2-oxyimino)-2-(2-aminothiazol-4-yl) acetic acid was then added thereto, followed by further stirring the resulting solution for one hour. After cooling down the stirred solution to a temperature of −15° C. to −20° C., anhydrous hydrochloric acid was introduced at a rate of 500 ml/min. to 1,000 ml/min over one hour, followed by stirring the solution. Upon this stirring, the deprotection on the carboxy group was proceeded while beginning to deposit a solid material. The solid material was filtered, washed with 100 ml of dicholoromethane, and 100 ml of diethyl ether, in sequence, and then dried in vacuo, thereby yielding 85 g (86% yield) of the title compound as a white solid. Melting point (° C.): 153–158 (decomposition); ¹NMR: (δ, DMSO-d₆); 1.51(s, 6H), 7.19(s, 1H).

EXAMPLE 2

Preparation of (Z)-2-(2-carboxymethoxyimino)-2-(2-aminothiazol-4-yl)acetylchloride monohydrochloride To 500 ml of dichloromethane, 65 g of phosphorus pentachloride was added and then stirred for 10 minutes. After this, 100 g of (Z)-2-(2-carboxymethoxyimino)-2-(-aminothiazol-4-yl)acetic acid was added thereto, and then stirred at a temperature of 0° C. to 5° C. for one hour. Next, 30 ml of a 70% perchloric acid solution was added dropwise to the stirred solution, followed by stirring for 30 minutes. Then, after 100 ml of diethyl ether and 100 ml of m,p-cresol were added to the stirred solution, the resulting solution was stirred for one hour. Afterwards, the produced solid material was filtered, washed with 100 ml of diethyl ether, and with 100 ml of dichloromethane, in sequence, and then dried at room temperature in vacuo overnight, thereby yielding 85 g (86% yield) of the title compound as a white solid. Melting point (° C.): 132–134 (decomposition); ¹NMR: (δ, DMS-d₆); 4.68(s, 2H), 7.07(s, 1H).

EXAMPLE 3

Preparation of 7-{2-(2-aminothiazol-4-yl)- 2-(Z)-(2-carboxyprop-2-oxyimino)acetamido}–3-(1-pyridiniummethyl)-ceph-3-em-4-carboxylate pentahydrate (ceftazidime pentahydrate)

This example illustrates the preparation of ceftazidime pentahydrate using the crystalline aminothiazole derivatives of the present invention.

To 100 ml of dichloromethane, 10 g of 7-amino-3-(1-pyridiniummethyl)-ceph-3-em-4-carboxylate hydroiodide was added, and 4 ml of triethylamine was then added dropwise at a temperature of 0 to 10° C. to ensure the dissolution of the hydroiodide. To which, (Z)-(2-carboxyprop-2-oxyimino)-2-(2-aminothiazole-4-yl)-acetylchloride monohydrochloride prepared in Example 1 was added three or four times for 30 minutes in such a fashion that the totally added amount thereof corresponds to 9.4 g. The resulting mixture was then stirred at a temperature of 0 to 10° C. for 30 minutes. The stirred solution was added with 50 ml of water to be separated into two layers. Next, an aqueous layer was collected, to which 2 g of activated carbon was then added. The solution was stirred for 30 minutes, and the stirred solution was filtered by a siliceous earth to remove the activated carbon. The resulting solution was adjusted to pH 3.8 with a 2N-hydrochloric acid solution, and left to stand at 5° C. for 12 hours. Next, the produced crystal was filtered, and washed with ice-water and acetone, in sequence, and then dried, thereby giving 12.1 g (80% yield) of the title compound as a white solid. ¹NHR :(d, DMSO-d₆):9.5(d, 1H, —CONH—), 9.4(d, 2H, pyridinium proton), 8.6(t, 2H, pyridinium proton), 8.2(t, 2H, pyridinium proton), 7.3(s, 2H, —NH₂), 6.7(s, 1H, amino-thiazole proton), 5.7(dd, 1H, C₇—H), 5.5(ABq, 2H, —CH₂—), 5.1(d, 1H, C₆—H), 3.3(ABq, 2H, C₂—H), 1.4(s, 6H, —C(CH₃)₂).

Comparative Example 1

Preparation of (6R, 7R)-7-{2-(2-aminothiazol-4-yl)-2-(Z)-(2-carboxyprop-2-oxyimino) acetamido}-3-(1-pyridiniummethyl)-ceph-3-em-4-carboxylate pentahydrate (ceftazidime pentahydrate)

This example illustrates the preparation of ceftazidime pentahydrate using the reactive derivative of 2-aminothiazole carboxylic acid of the prior art, according to processes described in Example 1 of U.S. Pat. No. 5,182,383 and Example 2 of U.S. Pat. No. 4,954,624.

12 g of 2-(2-amino-4-thiazolyl)-(Z)-2-[(1-tert-butoxycarbonyl-1-methylethoxy)imino]thioacetic acid-5-benzothiazol-2-yl-ester, 7.7 g of (6R,7R)-7-amino-3-(1-pyridiniummethyl)-ceph-3-em-4-carboxylate monohydrochloride monohydrate and 3.8 ml of triethylamine was added to a mixture of 75 ml of dichloromethane and 5 ml of methanol and then stirred for 10 hours at 0° C. The produced solid substance was filtered off, washed with a small amount of dichloromethane and then dried under vacuum at room temperature. Next, the resulting solid substance was added at a temperature of 0° C. to 5° C. to 15 ml of concentrated hydrochloric acid, to produce a light yellow-greenish solution. This solution was stirred for about 1 hour at 5° C. Then, 22.4 ml of ice water was added, followed by solid sodium bicarbonate, until the pH of the solution reached 4.0–4.1. The temperature was maintained at below 5° C. The mixture was then left to stand at a temperature of about 10° C. to 15° C., such that the product began to be crystallized. After this, the pH was adjusted to 3.6 with a 3N hydrochloric acid, and the mixture was left to stand for a further 5 hours at a temperature of 0° C. to 4° C. Then, the title compound was separated, washed with cold water and acetone, and dried, thereby yielding 7.73 g of the title compound in a pure form. Yield: 54.6%

The compound according to the present invention has the form of the pure, stable and crystalline acid halide. Thus, when this acid halide is used in the acylation with the 3-cephem compound for the preparation of the cephalosporin antibiotics, the acylation result in little or no production of the unnecessary impurities, such that the cephalosporin antibiotic can be obtained in a high purity. In addition to this advantage, as described in Example 3 and Comparative Example, the use of the compound of the present invention in the acylation allows the cephalosporin antibiotic to be obtained directly after the acylation without the deprotection step. Thus, the compound of the present invention allows the cephalosporin antibiotics to be obtained in higher yield and in a more economical manner, as compared with those of the prior art.

As apparent from the above description and Examples, the present invention provides the compound in the form of a pure, stable and crystalline form, from which various protecting groups were removed and which will be acylated by reaction with the 3-cephem compound. Therefore, the use of the acid halide of the present invention in the acylation with the 3-cephem compound allows the cephalosporin antibiotics, including ceftazime and cefixime, etc. to be prepared with little or no production of by-products.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A crystalline aminothiazole derivative represented by the following formula (I):

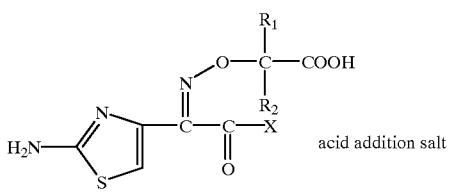

wherein $R_1$ and $R_2$ are the same or different and independently represent H, an alkyl group of 1 to 4 carbon atoms, or a cycloalkyl group of 3 to 5 carbon atoms, etc., X represents chlorine or bromine, and the acid in the acid addition salt represents an inorganic acid selected from the group consisting of hydrochloric acid, hydrobromic acid, sulfuric acid, hydroiodic acid, and perchloric acid, or an organic acid selected from the group consisting of formic acid, acetic acid, trifluoroacetic acid, propionic acid, methanesulfonic acid, and benzenesulfonic acid.

2. The crystalline aminothiazole derivative according to claim 1, which is (Z)-2-(2-carboxyprop-2-oxyimino)-2-(2-aminothiazol-4-yl)acetylchloride monohydrochloride having the following Debye-Scherrer X-ray powder diffraction pattern:

| $2\theta$ | d | $I/I_0$ |
|---|---|---|
| 6.46 | 13.67 | 297 |
| 12.88 | 6.87 | 173 |
| 16.10 | 5.50 | 103 |
| 18.52 | 4.79 | 1000 |
| 19.34 | 4.59 | 414 |
| 19.96 | 4.44 | 847 |
| 20.58 | 4.31 | 226 |
| 22.48 | 3.95 | 141 |
| 22.92 | 3.88 | 102 |
| 23.20 | 3.83 | 149 |
| 24.98 | 3.56 | 505 |
| 28.92 | 3.08 | 228 |
| 30.58 | 2.92 | 352 |
| 31.74 | 2.81 | 114 |
| 32.52 | 2.75 | 304 |
| 38.80 | 2.31 | 112 |

$2\theta$: diffraction angle,
d: interplanar spacing, and
$I/I_0$: relative intensity.

3. The crystalline aminothiazole derivative according to claim 1, which is (Z)-2-(2-carboxymethoxyimino)-2-(2-aminothiazol-4-yl)acetylchloride monohydrochloride having the following Debye-Scherrer X-ray powder diffraction pattern:

| $2\theta$ | d | $I/I_0$ |
|---|---|---|
| 15.58 | 5.68 | 137 |
| 17.94 | 4.94 | 309 |
| 18.54 | 4.78 | 182 |
| 20.22 | 4.39 | 407 |
| 21.84 | 4.07 | 1000 |
| 22.16 | 4.01 | 811 |
| 23.46 | 3.79 | 153 |
| 23.96 | 3.71 | 389 |
| 25.82 | 3.45 | 309 |

-continued

| 2θ | d | I/I₀ |
|---|---|---|
| 27.76 | 3.21 | 130 |
| 30.12 | 2.96 | 252 |
| 30.50 | 2.93 | 121 |

2θ: diffraction angle,
d: interplanar spacing, and
I/I₀: relative intensity.

4. A process for the preparation of a compound represented by the following formula (I), comprising the steps of:

reacting an organic acid represented by the following formula (II) with an acid halogenating agent to produce a compound of the following formula (II-1); and adding an inorganic or organic acid to the compound (II-1), to remove a carboxy protecting group of the compound (II-1) while obtaining the compound of the formula (I) in the form of a crystalline acid addition salt:

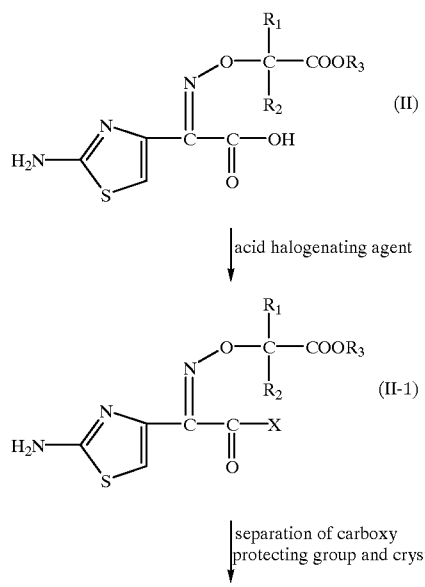

acid halogenating agent separation of carboxy protecting group and crystallization

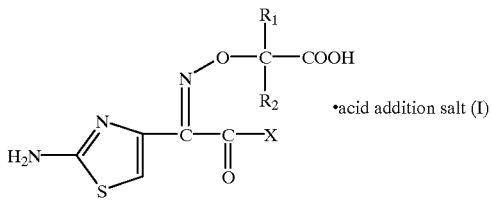

wherein $R_1$ and $R_2$ have the same meanings as defined in claim 1, and $R_3$ represents a carboxy protecting group selected farom the group consisting of t-butyl and diphenylmethyl.

5. The method according to claim 4, in which the acid halogenating agent is selected from the group consisting of phosphorus oxychloride, phosphorus pentachloride, phosphorus trichloride, phosphorus tribromide, thionyl chloride, and oxalyl chloride.

6. The method according to claim 4, in which the acid used for removing the carboxy protecting group is an inorganic acid selected from the group consisting of hydrochloric acid, hydrobromic acid, sulfuric acid, hydroiodic acid, and perchloric acid, or an organic acid selected from the group consisting of formic acid, acetic acid, trifluoroacetic acid, propionic acid, methanesulfonic acid, and benzenesulfonic acid.

7. The method according to claim 6, in which the removal of the carboxy protecting group is carried out in the presence of a cation trapping agent which is chosen from the group consisting of phenol, mp-cresol, and anisole, depending on the nature of the protecting group to be removed.

8. The method according to claim 4, in which the removal of the carboxy protecting group is carried out in a state where the compound of formula (II-1) is isolated from, or present in a reaction solution.

* * * * *